US012642437B2

(12) United States Patent
Chowdhury et al.

(10) Patent No.: US 12,642,437 B2
(45) Date of Patent: Jun. 2, 2026

(54) PERSONAL CAROTID ARTERY STENOSIS DETECTION AND STROKE PREVENTION DEVICE AND PROCESS

(71) Applicants:Aneeq Chowdhury, Portland, OR (US); Ehan Masud, Portland, OR (US)

(72) Inventors: Aneeq Chowdhury, Portland, OR (US); Ehan Masud, Portland, OR (US)

( * ) Notice: Subject to any disclaimer, the term of this patent is extended or adjusted under 35 U.S.C. 154(b) by 0 days.

(21) Appl. No.: 18/829,929

(22) Filed: Sep. 10, 2024

(65) Prior Publication Data

US 2025/0194929 A1 Jun. 19, 2025

Related U.S. Application Data

(60) Provisional application No. 63/610,589, filed on Dec. 15, 2023.

(51) Int. Cl.
A61B 5/00 (2006.01)
G06T 7/00 (2017.01)

(52) U.S. Cl.
CPC .......... A61B 5/0077 (2013.01); A61B 5/6887 (2013.01); A61B 5/7203 (2013.01); A61B 5/7264 (2013.01); G06T 7/0012 (2013.01); A61B 2560/045 (2013.01); G06T 2207/10016 (2013.01); G06T 2207/20024 (2013.01); G06T 2207/30104 (2013.01)

(58) Field of Classification Search
CPC .... A61B 5/0077; A61B 5/0064; A61B 5/7264
See application file for complete search history.

(56) References Cited

U.S. PATENT DOCUMENTS

| | | | |
|---|---|---|---|
| 2003/0091232 A1* | 5/2003 | Kalevo et al. ........... | G06K 9/00 |
| | | | 382/167 |
| 2016/0050348 A1* | 2/2016 | Gibbons ................ | H04N 5/225 |
| 2021/0338147 A1* | 11/2021 | Blondek et al. ......... | A61B 5/00 |
| 2021/0377490 A1* | 12/2021 | McNelley et al. ....... | H04N 7/15 |

(Continued)

OTHER PUBLICATIONS

Tsai et al., "Detection of Carotid Artery Stenosis Based on Video Motion Analysis for Fast Screening", 2022, J Am Heart Assoc. vol. 11, Issue 17 (Year: 2022).*

(Continued)

*Primary Examiner* — Anne M Kozak
*Assistant Examiner* — Kaitlyn Eunji Kim
(74) *Attorney, Agent, or Firm* — Plager Schack LLP; Mark H. Plager; Stephen Hallberg

(57) ABSTRACT

A personal carotid artery stenosis detection and stroke prevention device and a personal carotid artery stenosis detection and stroke prevention process are disclosed. The personal carotid artery stenosis detection and stroke prevention device is configured to check carotid arteries of a person for buildup of stenosis. The device is a smart device with a camera and a processing unit configured to analyze video footage captured by the camera and detect possible buildup of stenosis in one carotid artery or both carotid arteries. Analysis and detection is carried out according to the personal carotid artery stenosis detection and stroke prevention process. By detecting stenosis buildup, the device is able to inform the person of the risk of stroke, thereby helping the person to prevent a potential stroke.

15 Claims, 6 Drawing Sheets

(56) References Cited

U.S. PATENT DOCUMENTS

2022/0006813 A1* 1/2022 Jorasch et al. .......... H04L 29/06

OTHER PUBLICATIONS

Salvi et al., "Bodytune: Multi Auscultation Device—Personal Health Parameter Monitoring at Home", 2021, Current Directions in Biomedical Engineering. 7(2): 5-8 (Year: 2021).*

Tang et al., "Selective Search and Intensity Context Based Retina Vessel Image Segmentation", 2017, J Med Syst, 41:47 (Year: 2017).*

* cited by examiner

10

12

14A
14B
18
16
16
18

10

18
14A
14B
16
16
20
18

PERSONAL CAROTID ARTERY STENOSIS DETECTION AND STROKE PREVENTION DEVICE AND PROCESS

CLAIM OF BENEFIT TO PRIOR APPLICATION

This application claims benefit to U.S. Provisional Patent Application 63/610,589, entitled "A PERSONAL CAROTID ARTERY STENOSIS DETECTION AND STROKE PREVENTION DEVICE THAT IS CONFIGURED TO CHECK CAROTID ARTERIES OF A PERSON FOR BUILDUP OF STENOSIS," filed Dec. 15, 2023. The U.S. Provisional Patent Application 63/610,589 is incorporated herein by reference.

BACKGROUND

Embodiments of the invention described in this specification relate generally to medical imaging devices and systems, and more particularly, to a personal carotid artery stenosis detection and stroke prevention device that is configured to check carotid arteries of a person for buildup of stenosis.

Current devices that detect carotid artery stenosis are expensive and difficult to use, making them inaccessible to many. They are also mainly used after a stroke occurs. Furthermore, these existing carotid artery stenosis detection devices are mainly used after a stroke occurs. Thus, a person who wishes to prevent possible stroke by proactively monitoring potential buildup of stenosis in his or her own carotid arteries is left with no solution because the current methods to detect carotid artery stenosis are expensive and inaccessible from beyond a hospital, thus not being as helpful when detecting strokes due to carotid artery stenosis.

Therefore, what is needed is an inexpensive and accessible device that allows a person to check for potential stenosis buildup in their own carotid arteries on a regular basis and at any location, such as at home or work, instead of having to schedule and visit medical specialists for the same.

BRIEF DESCRIPTION

A personal carotid artery stenosis detection and stroke prevention device and a personal carotid artery stenosis detection and stroke prevention process are disclosed.

In some embodiments, the personal carotid artery stenosis detection and stroke prevention device is configured to check carotid arteries of a person for buildup of stenosis. In some embodiments, the personal carotid artery stenosis detection and stroke prevention device is a smart device with a camera and a processing unit configured to analyze video footage captured by the camera and detect possible buildup of stenosis in one carotid artery or both carotid arteries. By detecting stenosis buildup, the personal carotid artery stenosis detection and stroke prevention device is able to inform the person of the risk of stroke, thereby helping the person to prevent a potential stroke. Also, the personal carotid artery stenosis detection and stroke prevention device is extremely low-cost and user-friendly, which allows for wide, personal usage of such device by anyone and also allowing routine checks for potential stenosis buildup. Furthermore, the personal carotid artery stenosis detection and stroke prevention device is configured to detect any other artery blockage problems beyond carotid artery stenosis.

In some embodiments, the personal carotid artery stenosis detection and stroke prevention device comprises (i) a small form factor video camera configured to capture video in a high resolution format when a user utilizes the device to check for potential carotid artery stenosis buildup, (ii) lighting comprising at least one light that illuminates while the video camera captures the video and the user utilizes the device, (iii) exterior surface and edge foam strips (or foam blocks) that provide soft, cushioning exterior to apply to a carotid artery neck area of the user, (iv) a housing that encapsulates the video camera and the lighting, (v) a software program or mobile application ("mobile app") that implements a carotid artery stenosis detection algorithm that performs an analysis of videos captured in different areas of the user's neck by the video camera and compares color intensity of the video images (frames) in order to detect potential buildup of carotid artery stenosis, and (vi) a compute unit with a processor, such as a mobile device on which the mobile app executes at runtime or a single board computer with an embedded software program that includes runtime instructions for software program. In some embodiments, the personal carotid artery stenosis detection and stroke prevention device further comprises a plurality of LED lights. In some embodiments, the plurality of LED lights comprises the light and one or more other LED lights. In some embodiments, the video camera comprises a 4K video camera configured to capture video in 4K resolution at a minimum frame rate of thirty frames per second. In some embodiments, the 4K video camera is further configured to capture video in 4K resolution at a maximum frame rate of sixty frames per second. In some embodiments, the foam strips/foam block is made of EPS polystyrene. In some embodiments, the housing comprises a fabricated exterior shell with an aperture (opening) that is configured to hold the camera by inserting the camera into the aperture. In some embodiments, the fabricated exterior shell comprises a rigid 3D filament printed exterior shell.

In some embodiments, the personal carotid artery stenosis detection and stroke prevention process is a runtime process that is implemented in software and runs on a device that is communicably connected to the personal carotid artery stenosis detection and stroke prevention device. In some embodiments, the personal carotid artery stenosis detection and stroke prevention process starts when the user holds the personal carotid artery stenosis detection and stroke prevention device along their neck and starts the camera recording. In some embodiments, the personal carotid artery stenosis detection and stroke prevention process receives video data from the personal carotid artery stenosis detection and stroke prevention device as the camera records video. In some embodiments, the personal carotid artery stenosis detection and stroke prevention process receives the video data in real-time as the camera is recording the video. In some embodiments, the personal carotid artery stenosis detection and stroke prevention process analyzes the video data while receiving the real-time video data. To analyze the video data, the personal carotid artery stenosis detection and stroke prevention process of some embodiments (i) receives a top video clip captured by a camera of a personal carotid artery stenosis detection and stroke prevention device positioned along an upper area of a user's neck, (ii) receives a bottom video clip captured by the camera of the personal carotid artery stenosis detection and stroke prevention device positioned along a lower area of the user's neck, (iii) splits the top video clip into a plurality of top video clip frames and splits the bottom video clip into a plurality of bottom video clip frames, (iv) applies box blurring, by way of a linear spatial filter which is configured to spatially average the pixels in each frame in the top video clip frames and the bottom video clip frames to remove noise, (v) applies a Gaussian noise filter to remove remaining Gaussian noise from each frame in the top video clip frames and the bottom video clip frames, (vi) measures intensity of each frame after linear spatial filtering and Gaussian filtering are completed to remove noise, (vii) subtracts the highest and lowest intensities out of all the top filtered frames to calculate a total variation of intensity for the top filtered frames, (viii) subtracts the highest and lowest intensities out of all the bottom filtered frames to calculate a total variation of intensity for the bottom filtered frames, (ix) compares the total variation of intensity for the top filtered frames to the total variation of intensity for the bottom filtered frames, and (x) detects whether stenosis is present based on the comparison of the total variation of intensities for the top and bottom filtered frames, such that stenosis is affirmatively detected when the total variation of intensity for the bottom filtered frames is significantly higher than the total variation of intensity for the top filtered frames.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

Figure 1:
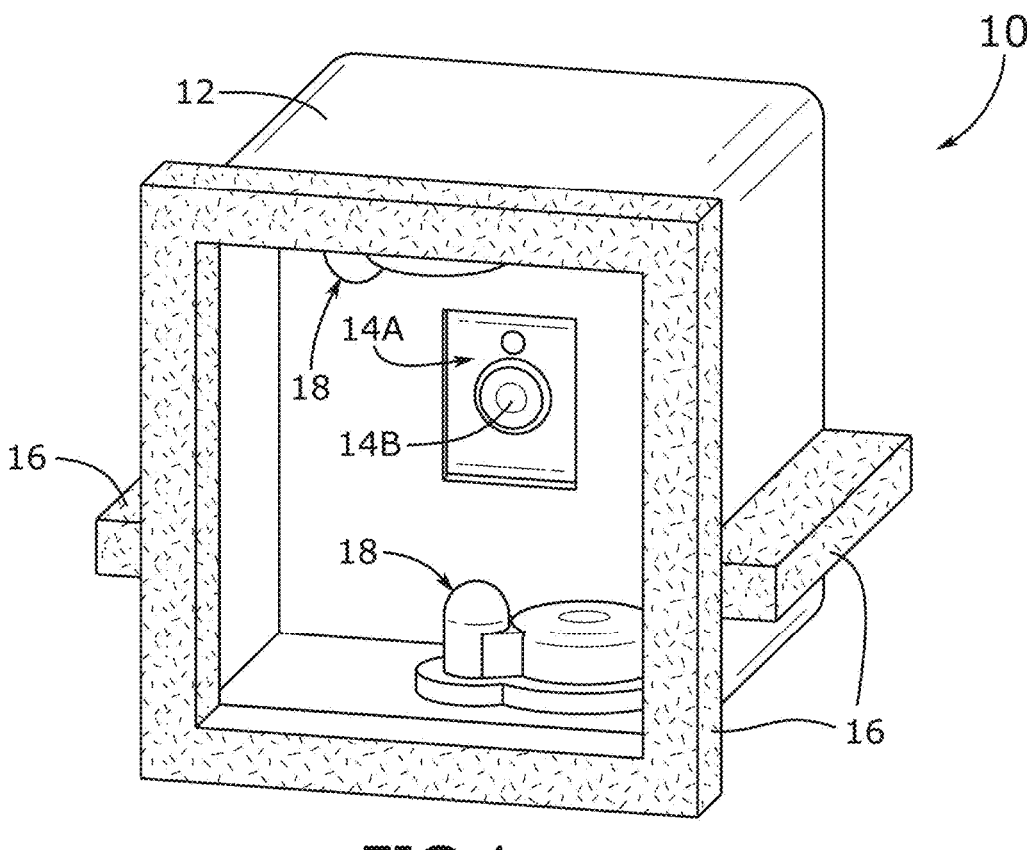
FIG. 1 conceptually illustrates a front perspective view of a personal carotid artery stenosis detection and stroke prevention device in some embodiments.

In the following detailed description of the invention, numerous details, examples, and embodiments of the invention are described. However, those skilled in the art will recognize that changes in modifications can be made to the exemplary embodiments without departing from the scope of the present disclosure. As used herein, the terms "comprises," "comprising," "includes," "including" and/or any other variation thereof, are intended to cover a non-exclusive inclusion, such that a system, process, method, article, and/or apparatus that comprises a list of elements does not include only those elements but can include other elements not expressly listed and/or inherent to such system, process, method, article, and/or apparatus.

It must also be noted that, as used in this specification and the appended claims, the singular forms "a," "an" and "the" include plural referents unless the content clearly dictates otherwise.

Also, all dimensions specified in this disclosure are by way of example only and are not intended to be limiting. Furthermore, the proportions shown in these Figures are not necessarily to scale. As will be understood by those of ordinary skill in the relevant art, the actual dimensions and proportions of any system, any device or part of a system or device disclosed in this specification will be determined by its intended use. Further to this, throughout the drawings, reference numbers are re-used to indicate correspondence between referenced elements.

Methods and devices that implement the embodiments of the various features of the invention will now be described with reference to the drawings. The drawings and the associated descriptions are provided to illustrate embodiments of the invention and not to limit the scope of the invention. Reference in the specification to "one embodiment", "an embodiment", or "some embodiments" is intended to indicate that a particular feature, structure, or characteristic described in connection with the embodiment or embodiments is included in at least one embodiment, and possibly multiple embodiments, of the invention. The appearances of the phrases "in one embodiment", "an embodiment", or "some embodiments" in various places in the specification are not necessarily all referring to the same embodiment.

Unless defined otherwise, all technical and scientific terms used herein have the same meaning as commonly understood by one of ordinary skill in the art to which the disclosure pertains. Although a number of methods and materials similar or equivalent to those described herein can be used in the practice of the present disclosure, certain preferred materials and methods are described herein.

The terms "first," "second," "third," "fourth," and the like in the description and in the claims, if any, are used for distinguishing between similar elements and not necessarily for describing a particular hierarchical, sequential, or chronological order. It is to be understood that the terms so used are interchangeable under appropriate circumstances such that the embodiments described herein are, for example, capable of operation in sequences other than those illustrated or otherwise described herein. Furthermore, the terms "comprise," "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

The terms "couple," "coupled," "couples." "coupling," and the like should be broadly understood and refer to connecting two or more elements or signals, electrically, mechanically, or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types. The absence of the word "removably," "removable," and the like near the word "coupled," and the like does not mean that the given coupling is or is not removable.

Similarly, the term "communicatively connected" and the like should be broadly understood and include physical hardware device and non-physical hardware device connections for data communications, whether the communication connection is a wireless connection, a wired connection, or a combination of both wireless and wired connections.

Figure 7:
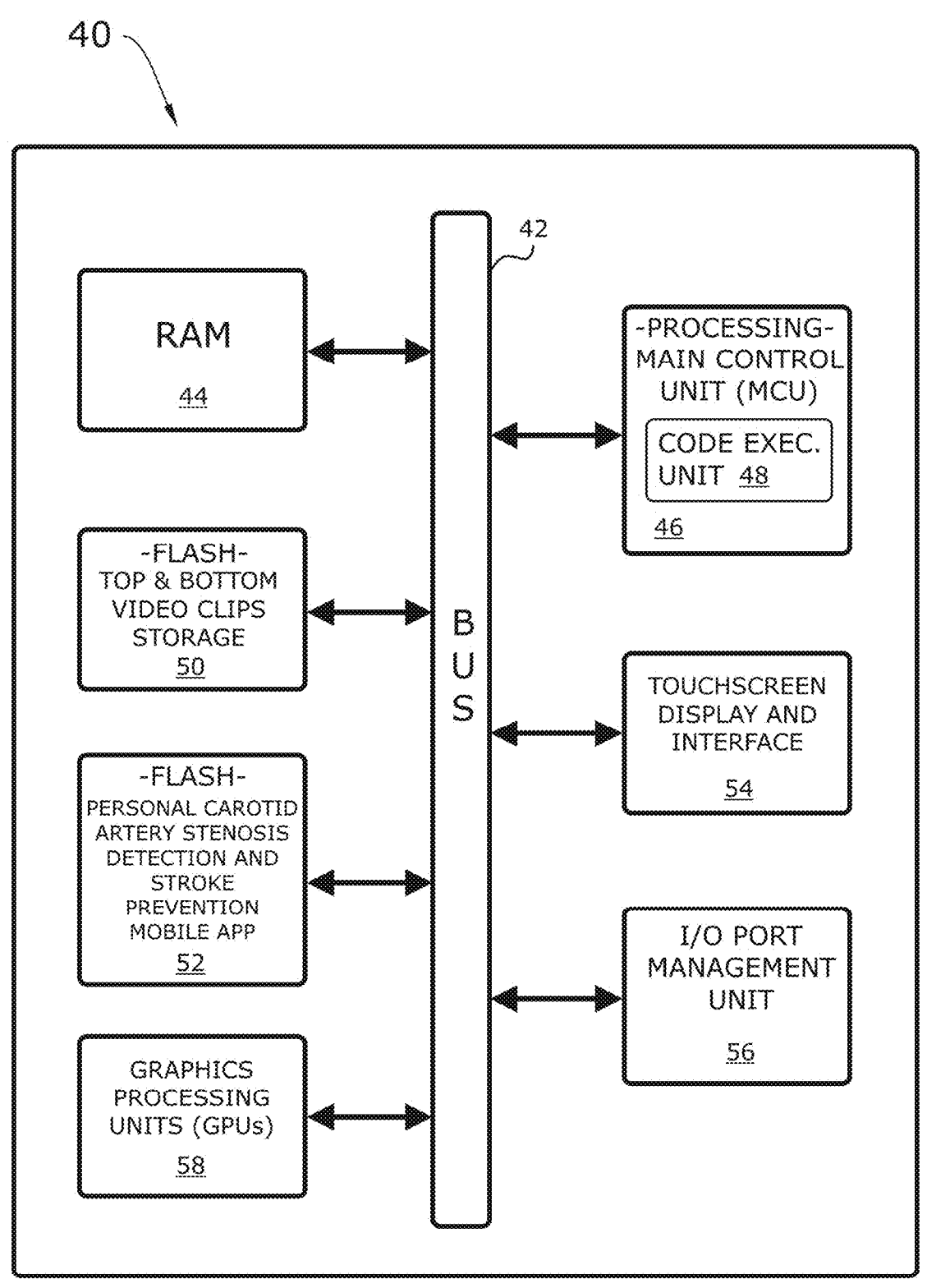
FIG. 7 conceptually illustrates a block diagram of a mobile device used, in connection with the personal carotid artery stenosis detection and stroke prevention device, to detect carotid artery stenosis in a user in some embodiments.
Figure 8:
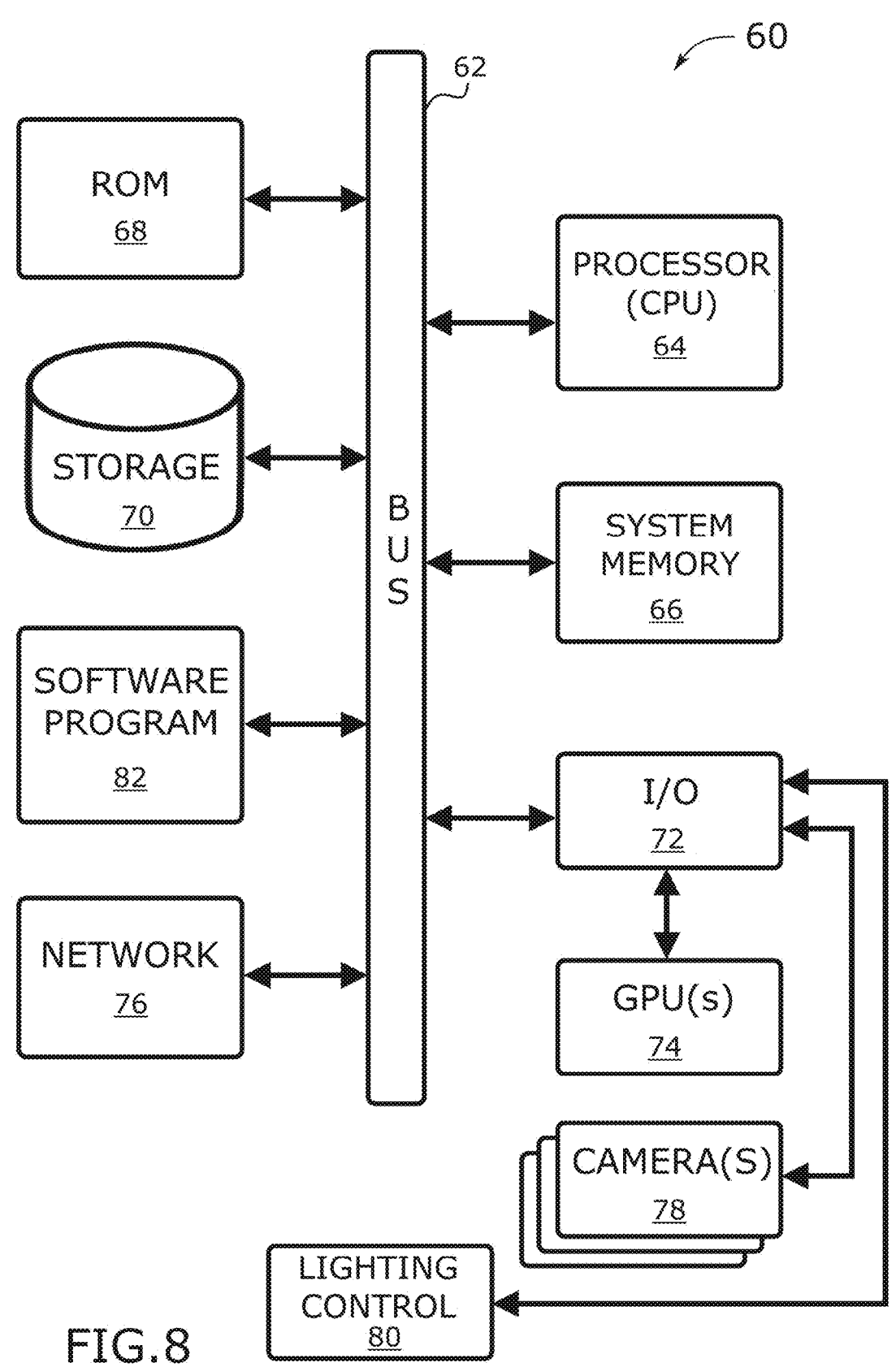
FIG. 8 conceptually illustrates a block diagram of an electronic system with which some embodiments of the invention are implemented.

Also, it is noted that the embodiments may be described as a process that is depicted as a flowchart, a flow diagram, a structure diagram, or a block diagram. For instance, a flow chart demonstrates conceptual "steps" of a process in FIG. 6 of the present specification, while FIGS. 7 and 8 illustrate block diagrams of architectures for various electronic systems, computing devices, mobile devices, or other such compute units that may be utilized in connection with the personal carotid artery stenosis detection and stroke prevention device of the present disclosure. The flowcharts and block diagrams in the figures can illustrate the architecture, functionality, and operation of possible implementations of systems, methods and computer programs according to various embodiments disclosed. In this regard, each block in the flowchart or block diagrams can represent a module, segment, or portion of code, that can comprise one or more executable instructions for implementing the specified logical function(s). It should also be noted that, in some alternative implementations, the functions noted in the blocks may occur out of the order noted in the figures. Although a flowchart may describe the operations as a sequential process, many of the operations can be performed in parallel or concurrently. In addition, the order of the operations may be rearranged. A process is terminated when its operations are completed. A process may correspond to a method, a function, a procedure, a subroutine, a subprogram, etc. When a process corresponds to a function, its termination corresponds to a return of the function to the calling function or the main function. Additionally, each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Moreover, a storage may represent one or more devices for storing data, including read-only memory (ROM), random access memory (RAM), magnetic disk storage mediums, optical storage mediums, flash memory devices and/or other non-transitory machine readable mediums for storing information. The term "machine readable medium" includes, but is not limited to, portable or fixed storage devices, optical storage devices, wireless channels and various other non-transitory mediums capable of storing, comprising, containing, executing or carrying instruction(s) and/or data.

Furthermore, embodiments may be implemented by hardware, software, firmware, middleware, microcode, or a combination thereof. When implemented in software, firmware, middleware or microcode, the program code or code segments to perform the necessary tasks may be stored in a machine-readable medium such as a storage medium or other storage(s). One or more than one processor may perform the necessary tasks in series, distributed, concurrently or in parallel. A code segment may represent a procedure, a function, a subprogram, a program, a routine, a subroutine, a module, a software package, a class, or a combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted through a suitable means including memory sharing, message passing, token passing, network transmission, etc., and are also referred to as an interface, where the interface is the point of interaction with software, or computer hardware, or with peripheral devices.

Specific embodiments of the invention described in this disclosure include a personal carotid artery stenosis detection and stroke prevention device. The personal carotid artery stenosis detection and stroke prevention device is configured to check carotid arteries of a person for buildup of stenosis. In some embodiments, the personal carotid artery stenosis detection and stroke prevention device is a smart device with a camera and a processing unit configured to analyze video footage captured by the camera and detect possible buildup of stenosis in one carotid artery or both carotid arteries. By detecting stenosis buildup, the personal carotid artery stenosis detection and stroke prevention device is able to inform the person of the risk of stroke, thereby helping the person to prevent a potential stroke. Furthermore, the personal carotid artery stenosis detection and stroke prevention device is configured to detect any other artery blockage problems beyond carotid artery stenosis.

In some embodiments, the personal carotid artery stenosis detection and stroke prevention device comprises (i) a small form factor video camera configured to capture video in a high resolution format when a user utilizes the device to check for potential carotid artery stenosis buildup, (ii) lighting comprising at least one light that illuminates while the video camera captures the video and the user utilizes the device, (iii) exterior surface and edge foam strips (or foam blocks) that provide soft, cushioning exterior to apply to a carotid artery neck area of the user, (iv) a housing that encapsulates the video camera and the lighting, (v) a software program or mobile application ("mobile app") that implements a carotid artery stenosis detection algorithm that performs an analysis of videos captured in different areas of the user's neck by the video camera and compares color intensity of the video images (frames) in order to detect potential buildup of carotid artery stenosis, and (vi) a compute unit with a processor, such as a mobile device on which the mobile app executes at runtime or a single board computer with an embedded software program that includes runtime instructions for software program. In some embodiments, the personal carotid artery stenosis detection and stroke prevention device further comprises a plurality of LED lights. In some embodiments, the plurality of LED lights comprises the light and one or more other LED lights. In some embodiments, the video camera comprises a 4K video camera configured to capture video in 4K resolution at a minimum frame rate of thirty frames per second. In some embodiments, the 4K video camera is further configured to capture video in 4K resolution at a maximum frame rate of sixty frames per second. In some embodiments, the foam strips/foam block is made of EPS polystyrene. In some embodiments, the housing comprises a fabricated exterior shell with an aperture (opening) that is configured to hold the camera by inserting the camera into the aperture. In some embodiments, the fabricated exterior shell comprises a rigid 3D filament printed exterior shell.

In some embodiments, the personal carotid artery stenosis detection and stroke prevention process is a runtime process that is implemented in software and runs on a device that is communicably connected to the personal carotid artery stenosis detection and stroke prevention device. In some embodiments, the personal carotid artery stenosis detection and stroke prevention process starts when the user holds the personal carotid artery stenosis detection and stroke prevention device along their neck and starts the camera recording. In some embodiments, the personal carotid artery stenosis detection and stroke prevention process receives video data from the personal carotid artery stenosis detection and stroke prevention device as the camera records video. In some embodiments, the personal carotid artery stenosis detection and stroke prevention process receives the video data in real-time as the camera is recording the video. In some embodiments, the personal carotid artery stenosis detection and stroke prevention process analyzes the video data while receiving the real-time video data. To analyze the video data, the personal carotid artery stenosis detection and stroke prevention process of some embodiments (i) receives a top video clip captured by a camera of a personal carotid artery stenosis detection and stroke prevention device positioned along an upper area of a user's neck, (ii) receives a bottom video clip captured by the camera of the personal carotid artery stenosis detection and stroke prevention device positioned along a lower area of the user's neck, (iii) splits the top video clip into a plurality of top video clip frames and splits the bottom video clip into a plurality of bottom video clip frames, (iv) applies box blurring, by way of a linear spatial filter which is configured to spatially average the pixels in each frame in the top video clip frames and the bottom video clip frames to remove noise, (v) applies a Gaussian noise filter to remove remaining Gaussian noise from each frame in the top video clip frames and the bottom video clip frames, (vi) measures intensity of each frame after linear spatial filtering and Gaussian filtering are completed to remove noise, (vii) subtracts the highest and lowest intensities out of all the top filtered frames to calculate a total variation of intensity for the top filtered frames, (viii) subtracts the highest and lowest intensities out of all the bottom filtered frames to calculate a total variation of intensity for the bottom filtered frames, (ix) compares the total variation of intensity for the top filtered frames to the total variation of intensity for the bottom filtered frames, and (x) detects whether stenosis is present based on the comparison of the total variation of intensities for the top and bottom filtered frames, such that stenosis is affirmatively detected when the total variation of intensity for the bottom filtered frames is significantly higher than the total variation of intensity for the top filtered frames.

As stated above, current devices that detect carotid artery stenosis are expensive and difficult to use, making them inaccessible to many. Furthermore, these existing carotid artery stenosis detection devices are mainly used after a stroke occurs. Thus, a person who wishes to prevent possible stroke by proactively monitoring potential buildup of stenosis in his or her own carotid arteries is left with no solution because the current methods to detect carotid artery stenosis are expensive and inaccessible from beyond a hospital, thus not being as helpful when detecting strokes due to carotid artery stenosis. Embodiments of the personal carotid artery stenosis detection and stroke prevention device described in this specification solve such problems by way of a user-friendly and low-cost device that is able to detect stenosis buildup in carotid arteries with high accuracy, thereby providing a solution that allows for wide-spread, accessible detection for all people, regardless of socioeconomic status.

Embodiments of the personal carotid artery stenosis detection and stroke prevention device described in this specification differ from and improve upon currently existing options. In particular, the existing devices are costly to employ due to their designs and materials. Consequently, most people do not have regular access to carotid artery stenosis detecting devices and, therefore, are unable to monitor one aspect of health that could lower their risk for stroke. By contrast, the personal carotid artery stenosis detection and stroke prevention device described in this specification is a low-cost and easy-to-use device that provides a way for virtually anyone to monitor their own potential buildup of carotid artery stenosis. The personal carotid artery stenosis detection and stroke prevention device is a smart device, that is smaller, cheaper, and easier to use than the currently existing devices/systems. The personal carotid artery stenosis detection and stroke prevention device is built on a unique combination of software (which performs a runtime detection algorithm process, also referred to as the "personal carotid artery stenosis detection and stroke prevention process") and hardware components. In particular, the detection algorithm analyzes the video captured by the camera. The analysis involves checking for color intensity variation, which none of the existing devices or systems do. This allows the personal carotid artery stenosis detection and stroke prevention device to embed any camera, including even a low cost camera, and still produce highly accurate results. In this way, the personal carotid artery stenosis detection and stroke prevention device is able to detect and prevent a potential stroke when carotid artery stenosis buildup is detected.

The personal carotid artery stenosis detection and stroke prevention device of the present disclosure may be comprised of the following elements. This list of possible constituent elements is intended to be exemplary only and it is not intended that this list be used to limit the personal carotid artery stenosis detection and stroke prevention device of the present application to just these elements. Persons having ordinary skill in the art relevant to the present disclosure may understand there to be equivalent elements that may be substituted within the present disclosure without changing the essential function or operation of the personal carotid artery stenosis detection and stroke prevention device.

1. Lighting—button lights, LED lamp/lighting, or other small form factor lighting that is secure to an interior area of the device (e.g., lightweight, ultra small, ultra bright LED utility lights, also referred to as "button lamps").

2. Camera (e.g., a high-definition camera capable of recording video at at least thirty frames per second or an ultra-high definition camera, such as (but not exclusively) a 4K Spy Camera Hidden Camera, Ebarsenc UHD WiFi Wireless Mini Camera/Battery Operated Nanny Cam/Small Camera for Home Security/Indoor Camera with Motion Detection Night Vision/Surveillance Camera).

3. A device housing (or shell) with interior surface space for the LED lighting and the camera. The device housing may be fabricated by 3D printing process using 3D printer filament.

4. Glue/adhesive (e.g., glue sticks). Optionally applied to button lights and/or camera to attached to device housing, but may be any other suitable attachment mechanism.

5. Foam strips for cushioning or a foam block with size dimensions of 6×12×1 or other small form factor and made of any sort of foam that provides soft cushioning (e.g., an EPS polystyrene block).

6. Embedded software program (code) that is developed in any development environment on a computing device (such as a laptop computer, desktop computer, or other computing device). In a some embodiments, a Python IDE is utilized. In a preferred embodiment, the Python IDE is PyCharm IDE, which is used in conjunction with one or more PyCharm Python libraries for development of the embedded program which carries out the runtime operations/process.

7. Software program and/or mobile application (or "mobile app"). The software program and/or mobile app may include instructions for completing the stenosis detection algorithm. Furthermore, the mobile app provides the user-facing software implementation which is configured to display the results after performing the runtime operations/process and also may provide additional user experience and user control interactions.

The housing/shell of the personal carotid artery stenosis detection and stroke prevention device is fabricated in a shape similar to a box with an open end placed to the user's neck and a back-side panel that is opposite the open end with an empty space within (otherwise referred to as a hole, an aperture, a carve-out, a cut-out, and the like) for the camera and camera lens. The camera and lens face the open end such that the camera can capture video of the user's neck while the lighting is illuminated and the device is held up to the user's neck. The lighting is secure to the interior of the box-like area of the device housing/shell with a strong adhesive, such as hot glue (from glue sticks via glue stick gun), or alternative adhesives that secure the LED lights to the interior of the device housing/shell. The camera may be secured with adhesive once inserted into the aperture, but in some embodiments, the camera fits snug within the aperture such that it can be inserted and removed with some manual force, but is stable during video capture. The foam block/ foam strips provides soft, cushioning surface for a user of the device, allowing the user to comfortably apply the device to their neck. The underlying Python/Pycharm code of the embedded software program (implemented in the mobile app) has instructions for utilizing the camera video footage captured by the user when the device is applied to their neck.

The personal carotid artery stenosis detection and stroke prevention device of the present disclosure generally works by checking for a difference of 0.25 in intensity changes (also referred to as "intensity variation") between the top and bottom half of the neck (e.g., of one side of the neck, or, as desired, both sides of the neck). A difference amounting to 0.25 or more is considered a threshold difference that indicates the bottom half intensity is significantly higher than the intensity of the frames/images in the top half. When there is such a difference of at least 0.25 detected, the device is able to conclude that there is stenosis.

To make the personal carotid artery stenosis detection and stroke prevention device of the present disclosure, a person may purchase or obtain the components commercially and then construct them into a whole device unit by fabricating the housing/shell (e.g., by 3D printing using 3D printer filament in a suitable 3D printer), coding the software (which implements the detection algorithm) for execution on a computing device (e.g., a mobile device, a single board computer, etc.), and attaching the camera and LEDs to the inner surface of the housing (via hot glue or another type of adhesive).

At its core, the personal carotid artery stenosis detection and stroke prevention device comprises (i) a camera configured to capture video of a neck area of a user, (ii) a housing structure comprising a plurality of panels comprising a camera plate with an opening/slot (or aperture) and at least one side panel (in a preferred embodiment, four side panels, to form a box-like shape) with a connecting edge and an open edge, wherein the connecting edge of the at least one side panel attaches to the camera plate, wherein the camera is oriented to capture video in a direction toward the open edge, (iii) lighting secured to the housing and configured to illuminate when the camera captures video of the neck area of the user, and (iv) foam cushioning that lines the open edge of the at least one side panel of the housing structure. In some embodiments, the light is a first light among a plurality of LED button lights of the personal carotid artery stenosis detection and stroke prevention device. In some embodiments, the camera is a small form factor video camera. In some embodiments, the camera is a high resolution format video camera. In some embodiments, the foam cushioning provides a soft, cushioning exterior to apply to the neck area of the user. In some embodiments, the neck area of the user to which the personal carotid artery stenosis detection and stroke prevention device is applied, positioned, placed, or otherwise held is a carotid artery neck area, along an exterior skin surface of the neck nearby where the carotid artery traverses vertically through the interior of the neck. In some embodiments, the neck area of the user to which the personal carotid artery stenosis detection and stroke prevention device is applied comprises two key areas along the carotid artery traversal route, namely, a top carotid artery neck area and a bottom carotid artery neck area. In some embodiments, the housing structure is created by 3D print out, namely by a rigid 3D filament printed exterior shell that is formed to sufficiently encapsulates the camera and the lighting. Other manners of making or manufacturing the housing structure are also supported including one in which a foam block is carved out in its interior to form a shell for placement and attachment of lights and camera, with an open end through which the camera is able to capture video of the user's neck. Whether foam block or rigid 3D filament printed exterior shell, the opposite side of the open end is a side to which the camera attaches (referred to as the "camera plate" or "camera side of housing"). The camera plate of some embodiments includes a hole, a space, a carve-out, a cut-out, an aperture, or some other form of space that is neither foam nor rigid 3D filament shell material, but through which the camera may be inserted to secure (or which otherwise holds the camera in place) while capturing video of the user's neck. These core components are demonstrated and described next, by reference to FIGS. 1-4.

Figure 2:
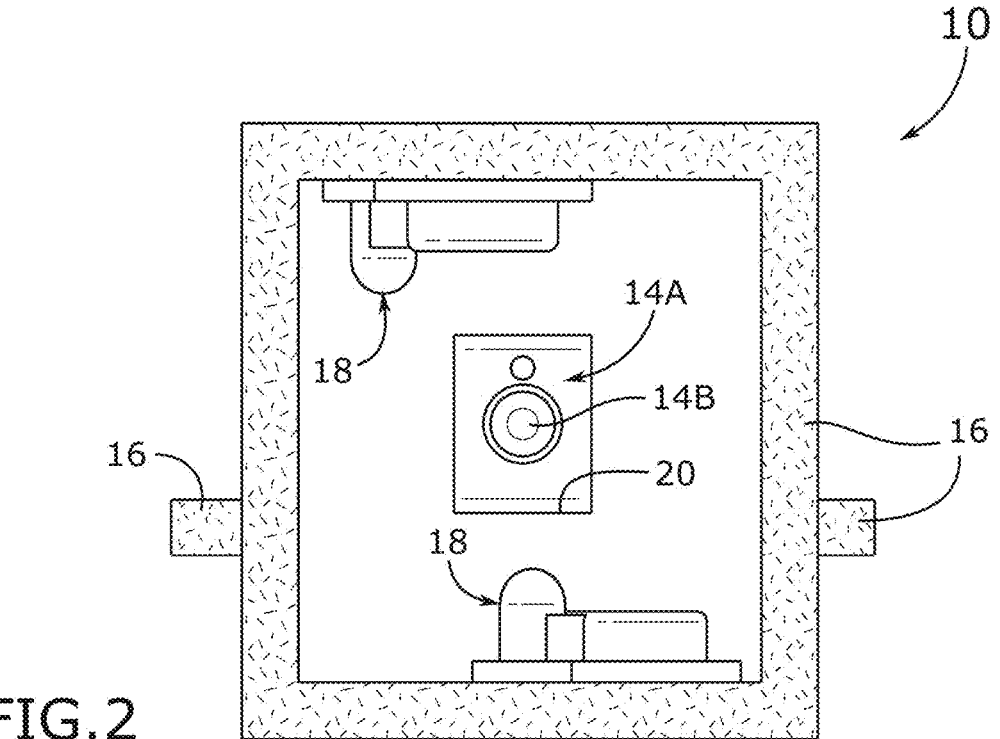
FIG. 2 conceptually illustrates a front view of the personal carotid artery stenosis detection and stroke prevention device in some embodiments.

Referring first to FIGS. 1-2, a personal carotid artery stenosis detection and stroke prevention device 10 is shown. Specifically, FIG. 1 conceptually illustrates a front perspective view of the personal carotid artery stenosis detection and stroke prevention device 10, while FIG. 2 conceptually illustrates a front view of the personal carotid artery stenosis detection and stroke prevention device 10. As shown in these figures, the personal carotid artery stenosis detection and stroke prevention device 10 includes a housing 12, a camera 14A, a camera lens 14B, a plurality of foam cushions 16, a plurality of lights 18, and a camera enclosure housing aperture 20 (referred to simply as the "camera enclosure 20").

In some embodiments, the housing 12 forms a main body component of the personal carotid artery stenosis detection and stroke prevention device 10. In some embodiments, the housing 12 forms an open box-like shape with an open end through which the camera 14A captures video as the plurality of lights 18 are illuminated and the personal carotid artery stenosis detection and stroke prevention device 10 is held up to the user's neck in an orientation with the open end placed directly to the skin of the user's neck. In some embodiments, the plurality of lights 18 comprise a plurality of LED lights (or "LEDs"). In some embodiments, the plurality of lights 18 comprise a plurality of button lights 18. In some embodiments, the plurality of lights 18 comprise a plurality of button LED lights 18 (or "button LEDs").

In some embodiments, the camera 14A comprises a video camera. In some embodiments, the camera 14A comprises a video camera configured to record high definition video. In some embodiments, the camera 14A comprises a video camera configured to record ultra-high definition video (referred to as "4K video" captured by a "4K video camera"). In some embodiments, the camera lens 14B is configured to provide a fixed focal length optimized to capture video at a macro-distance of approximately 1-5 inches. In some embodiments, the camera lens 14B is configured to automatically adjust a focal length to capture clear (non-blurry) video when the personal carotid artery stenosis detection and stroke prevention device 10 is held to the upper area of the user's neck. In some embodiments, the camera lens 14B is detachable from the camera 14A and can be replaced with another camera lens. In some embodiments, the camera lens 14B is detachable from the camera 14A and can be replaced with another lens.

In some embodiments, the foam cushions 16 are attached to exterior portions of the housing 12 to provide a soft surface for application of the personal carotid artery stenosis detection and stroke prevention device 10 to the user's neck. In some embodiments, the cushions 16 surround the edges of the open end of the housing 12. In some embodiments, the cushions 16 also include side cushions 16 that provide an effective grip for a user holding the personal carotid artery stenosis detection and stroke prevention device 10 during video recording.

Figure 3:
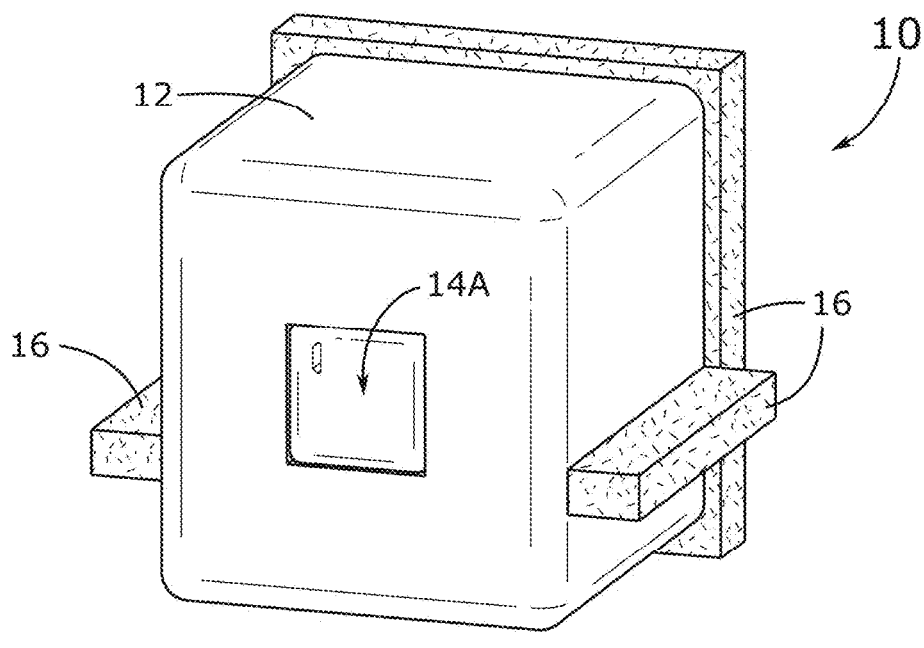
FIG. 3 conceptually illustrates a rear perspective view of the personal carotid artery stenosis detection and stroke prevention device in some embodiments.
Figure 4:
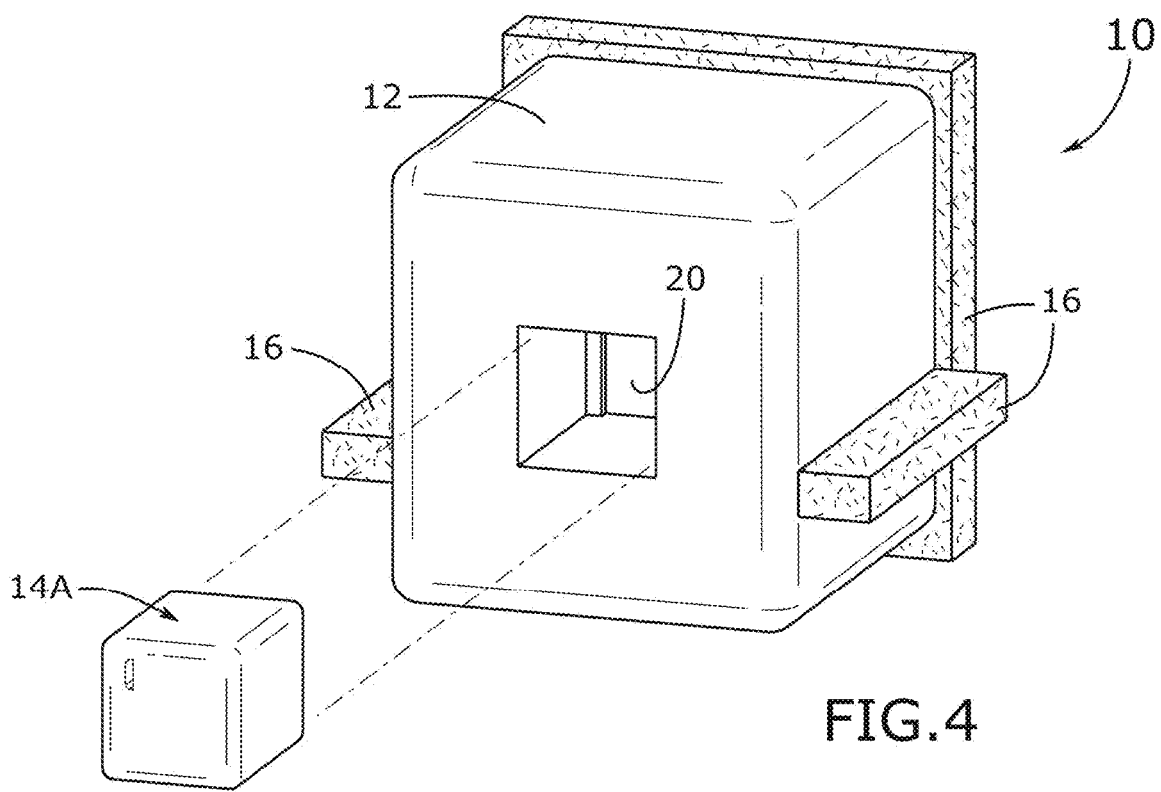
FIG. 4 conceptually illustrates an exploded rear perspective view of the personal carotid artery stenosis detection and stroke prevention device in some embodiments.

Rear views of the personal carotid artery stenosis detection and stroke prevention device 10 are shown in FIGS. 3-4. Specifically, FIG. 3 conceptually illustrates a rear perspective view of the personal carotid artery stenosis detection and stroke prevention device 10 and FIG. 4 conceptually illustrates an exploded rear perspective view of the personal carotid artery stenosis detection and stroke prevention device 10. In some embodiments, an aperture is carved out of a back side opposite the open end of the housing 12. In some embodiments, the aperture provides the camera enclosure 20. In some embodiments, the aperture is approximately a size that is sufficient to snuggly insert the camera 14A and lens 14B. As shown from rear views of the personal carotid artery stenosis detection and stroke prevention device 10, the camera 14A is capable of removal from the housing 12, by sliding the camera 14A (and camera lens 14B, not shown in these figures) out of the camera enclosure 20. As such, a user could install a different camera or simply remove the camera 14A to upload recorded video to the user's mobile device, a local storage, a laptop, a desktop computer, or for any other reason.

To use the personal carotid artery stenosis detection and stroke prevention device of the present disclosure, a user simply needs to hold the device to the side of their neck and start recording. Ideally, the user records a full 30-second video clip to ensure a sufficient number of frames for analysis. More specifically, the user would start the software implementation of the personal carotid artery stenosis detection and stroke prevention process and, when the program in running on the user's computing device, the user would capture video as the foam block area of the device is held up to his/her neck in view of the carotid artery (either side), and then illuminating the LEDs. The software implementation of the personal carotid artery stenosis detection and stroke prevention process may be any type of software to which the personal carotid artery stenosis detection and stroke prevention device can connect for video data transfer. In a preferred embodiment, the software implementation of the personal carotid artery stenosis detection and stroke prevention process is a mobile app (also referred to as the "personal carotid artery stenosis detection and stroke prevention mobile app") that runs on a mobile device, such as a smart phone, operated by the user. In some embodiments, the personal carotid artery stenosis detection and stroke prevention mobile app includes a user interface, multiple user tools, and an underlying detection algorithm or program that performs real-time processing of the video recording. The connection between the user's device and the personal carotid artery stenosis detection and stroke prevention device can be a hard-wired connection or a wireless connection. For wireless connections, the personal carotid artery stenosis detection and stroke prevention device may include an onboard communications module with one or more of a Bluetooth communications device, a WiFi communications device, a cellular communications device, or another wireless communications device. Similarly, the user's device would include sufficient communications hardware to establish and maintain a wireless connection with the personal carotid artery stenosis detection and stroke prevention device as the camera is streaming the video being recorded of the user's upper neck. The captured video is then received by the personal carotid artery stenosis detection and stroke prevention mobile app running on the user's mobile device and is available for processing and analysis by the detection algorithm (program) running on the device. The code of the detection algorithm for the personal carotid artery stenosis detection and stroke prevention mobile app checks for variations in color intensity between the bottom and top half of a given side of the neck. For example, a 30-second video is taken which is returned to the runtime program. In some embodiments, the detection program embedded within the personal carotid artery stenosis detection and stroke prevention mobile app involves a first set of steps for applying box blurring and Gaussian filters to particular frames in the video. The detection program then checks for the intensities in each frame, as well as finding the maximum and minimum intensity in the 30-second video. In some embodiments, the detection program subtracts the maximum and minimum intensities to obtain an overall change in intensity (variation in intensity). In some embodiments, the detection program may also perform other steps, such as subtracting the changes in intensity and determining whether the bottom half changes 0.25 or more in intensity than the top half. A difference amounting to 0.25 or more is considered a threshold difference that indicates the bottom half intensity is significantly higher than the intensity of the fames/images in the top half. When the threshold is met or exceeded (meaning the bottom half is significantly higher in intensity variation compared to the intensity variation for the top half), then stenosis is affirmatively detected as a result. A user can view results through the mobile app on their mobile device and, optionally, view results through the Pycharm IDE (e.g., on a connected laptop). An example of a user utilizing the personal carotid artery stenosis detection and stroke prevention device to record video is described below, by reference to FIG. 5. Another example of a runtime detection algorithm, performed by the personal carotid artery stenosis detection and stroke prevention mobile app (or other software implementation of the personal carotid artery stenosis detection and stroke prevention process), is described further below, by reference to FIG. 6.

Figure 5:
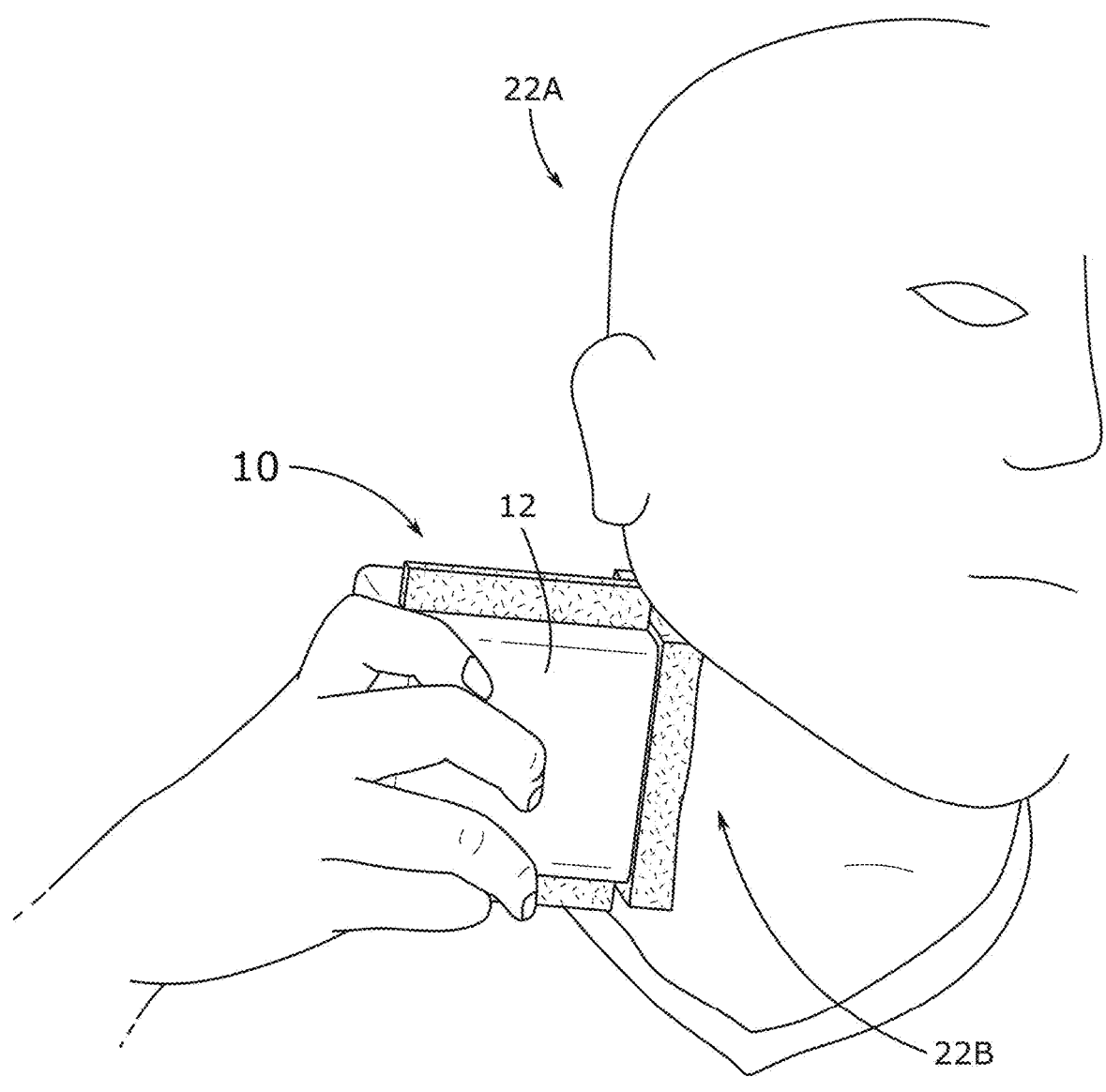
FIG. 5 conceptually illustrates a perspective view of the personal carotid artery stenosis detection and stroke prevention device being utilized by a user in some embodiments.

By way of example, FIG. 5 conceptually illustrates a perspective view of the personal carotid artery stenosis detection and stroke prevention device 10 being utilized by a user 22A. Specifically, the user 22A is holding the personal carotid artery stenosis detection and stroke prevention device 10 against the user's neck 22B, along a side of the neck 22B through which the carotid artery passes, which provides an optimal, but not requirement, placement position. Notably, the user 22A may hold the personal carotid artery stenosis detection and stroke prevention device 10 at positions that deviate from this optimal position along the neck 22B and the camera 14A can still capture the requisite video. Note that the personal carotid artery stenosis detection and stroke prevention device 10 shown in this figure appears to have a size that is approximately the same as the length of the neck 22B of the user 22A. In practice, the personal carotid artery stenosis detection and stroke prevention device 10 typically has a smaller form factor. However, for purposes of illustration, and not limitation, the personal carotid artery stenosis detection and stroke prevention device 10 is shown in this figure in this larger size.

After the user 22A positions the personal carotid artery stenosis detection and stroke prevention device 10 against the user's neck 22B, the user 22A would start recording. The actions that proceed during recording (and/or after recording) are encompassed in a set of detection algorithm steps referred to as the personal carotid artery stenosis detection and stroke prevention process (or the "personal carotid artery stenosis detection and stroke prevention runtime process"). The personal carotid artery stenosis detection and stroke prevention runtime process is described next, by reference to FIG. 6.

Figure 6:
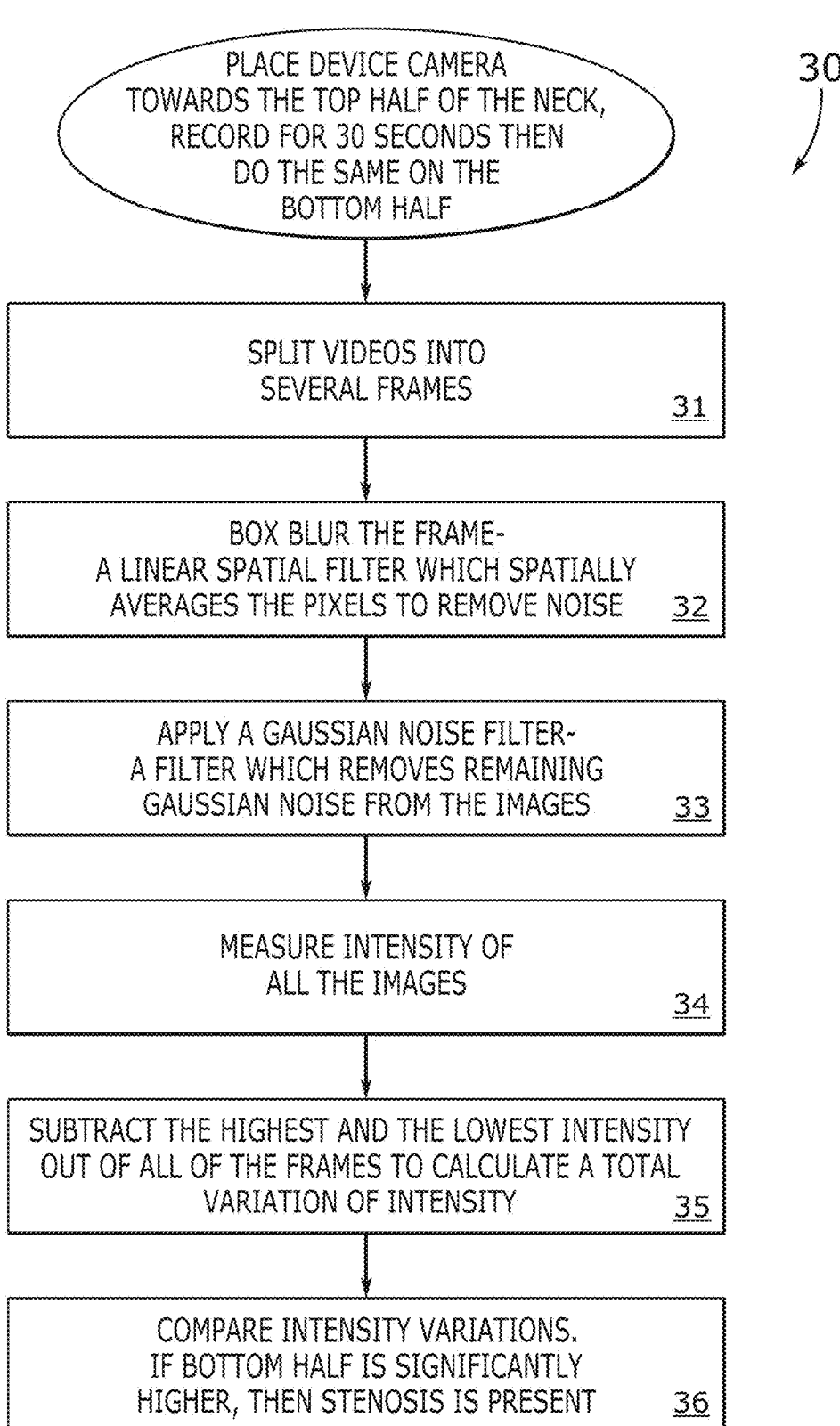
FIG. 6 conceptually illustrates a personal carotid artery stenosis detection and stroke prevention process in some embodiments.

Specifically, FIG. 6 conceptually illustrates a personal carotid artery stenosis detection and stroke prevention runtime process 30. Notably, the main actions involved in the personal carotid artery stenosis detection and stroke prevention runtime process 30 are performed by the user's connected device or by an embedded computing component of the personal carotid artery stenosis detection and stroke prevention device 10, such as a single board computer or a controller.

As a preliminary step of the personal carotid artery stenosis detection and stroke prevention runtime process 30, the personal carotid artery stenosis detection and stroke prevention device 10 is placed against the user's neck 22B in an orientation in which the camera 14A and camera lens 14B face towards the user's neck 22B. Ideally, the user 22A places the personal carotid artery stenosis detection and stroke prevention device 10 towards the top half of the neck 22B. Once the personal carotid artery stenosis detection and stroke prevention device 10 is in position against the neck 22B with the camera 14A and camera lens 14B facing the neck 22B, the user 22A starts the camera 14A recording video for a duration of time. In a preferred embodiment, the duration of time is approximately thirty seconds or more. After capturing a thirty-second video clip, the user 22A moves the personal carotid artery stenosis detection and stroke prevention device 10 to the bottom half of the neck 22B and records a second thirty-second video clip. In some embodiments, each of the two thirty-second video clips are recorded by the camera 14A and stored in onboard camera storage before processing of the video clips begins. In that case, the top and bottom thirty-second video clips are uploaded to the user's computing device before processing starts. In some other embodiments, the camera 14A is configured to stream the video clips to the user's computing device (e.g., mobile device) in real-time while each of the thirty-second video clips are being recorded. In still other embodiments, the personal carotid artery stenosis detection and stroke prevention device 10 includes an embedded single board computer (SBC), such as a Raspberry Pi, that is connected to the camera 14A and button lights 18 and is configured to receive the recorded video as a stream while the camera 14A captures the video for each of the top and bottom video clips.

After the top and bottom thirty-second video clips are captured, recorded, and made available to the detection algorithm on the user's computing device (or embedded computing device), the personal carotid artery stenosis detection and stroke prevention runtime process 30 starts analysis and processing of the video clips. Initially, the personal carotid artery stenosis detection and stroke prevention runtime process 30 splits each of the thirty-second video clips into several video frames (at 31). In some embodiments, the number of frames depends on a frame rate of recording the respective video clips. In some embodiments, the camera 14A is configured to record thirty frames per second. In some embodiments, the camera 14A is a 4K camera that is configured to record sixty frames per second. In some embodiments, the camera 14A is configured to record less than thirty frames per second. In some embodiments, the camera 14A is configured to record more than thirty frames per second and less than sixty frames per second. In some embodiments, the camera 14A is configured to record more than sixty frames per second. In some embodiments, the number of frames is a fraction of the frame rate of recording the respective video clips. For instance, if the camera 14A is configured to record thirty frames per second, the splitting of the video clip into several frames may involve the use of every third frame (amounting to a total of ten frames utilized for each one second thirty frame sequence), or configured to split the frames along another fraction.

After splitting (at 31) each of the top and bottom thirty-second video clips into their respective frames, the personal carotid artery stenosis detection and stroke prevention runtime process 30 applies box blurring of each frame (at 32). Specifically, a linear spatial filter is applied to each frame. The linear spatial filter is configured to spatially average the pixels in each frame to remove noise from the respective frame.

After applying box blurring to the frames (at 32), the personal carotid artery stenosis detection and stroke prevention runtime process 30 applies a Gaussian noise filter to the frames (at 33). The Gaussian noise filter is configured to remove Gaussian noise from the frames.

After applying the Gaussian noise filter to the frames (at 33), the personal carotid artery stenosis detection and stroke prevention runtime process 30 measures intensity of all the frames/images (at 34). Intensity is measured based on a relative intensity evident in each frame. Intensity may be a measurement of color intensity or illumination intensity.

Next, the personal carotid artery stenosis detection and stroke prevention runtime process 30 subtracts the highest and lowest intensity out of all the frames to calculate a total variation of intensity (at 35) across all of the frames in the top thirty-second video clip and the same for the bottom thirty second video clip.

Finally, the personal carotid artery stenosis detection and stroke prevention runtime process 30 compares the intensity variations between the frames in the top thirty-second video clip and frames in the bottom thirty-second video clip (at 36). By comparing the intensities, the personal carotid artery stenosis detection and stroke prevention runtime process 30 is able to determine whether the variation in intensity of the frames in the bottom thirty-second video clip is significantly higher than the variation in intensity of the top thirty-second video clip (at 36). Stenosis is present when the intensity of the frames in the bottom thirty-second video clip is significantly higher than the intensity of the frames in the top thirty-second video clip. On the other hand, stenosis cannot be confirmed by the personal carotid artery stenosis detection and stroke prevention runtime process 30 when the intensity of the frames in the bottom thirty-second video clip is not determined to be significantly higher than the intensity of the frames in the top thirty-second video clip.

As noted above, the personal carotid artery stenosis detection and stroke prevention device of some embodiments works in conjunction with a mobile application ("mobile app") that implements the detection algorithm. The detection algorithm, at its core, is configured to analyze video captured by the camera to detect potential buildup of carotid artery stenosis. That is, when the mobile app is running on a mobile device and the camera captures video of the user's neck, the mobile app analyzes and processes the captured videos to determine whether there is stenosis present or not. In some embodiments, the detection algorithm analyzes video captured by the camera based on a difference of color intensity between a top video clip captured by the camera along a top area of the neck and a bottom video clip captured by the camera along a bottom area of the neck. In some embodiments, the top video clip is a minimum duration of thirty seconds (i.e., a thirty-second top video clip and a thirty-second bottom video clip, since the top and bottom areas of the carotid artery are compared). In some embodiments, the detection algorithm involves several operations including (i) splitting the thirty-second top video clip into a plurality of top video frames, (ii) splitting the thirty-second bottom video clip into a plurality of bottom video frames, (iii) removing noise from the plurality of top video frames and the plurality of bottom video frames, (iv) measuring intensity of all video frames in the plurality of top video frames and the plurality of bottom video frames, (v) calculating a total top variation of intensity by subtracting a highest intensity measured in a highest intensity top video frame and a lowest intensity measured in a lowest intensity top video frame, (vi) calculating a total bottom variation of intensity by subtracting a highest intensity measured in a highest intensity bottom video frame and a lowest intensity measured in a lowest intensity bottom video frame, (vii) comparing the total bottom variation of intensity to the total top variation of intensity, and (viii) determining whether the total bottom variation of intensity is higher than a threshold difference higher than the total top variation of intensity. When the total bottom variation of intensity is significantly higher than the total top variation of intensity (e.g., 0.25 or more), then carotid artery stenosis is considered to be present. In some embodiments, the detection algorithm removes noise from the plurality of top video frames and the plurality of bottom video frames by applying box blurring to each frame. In some embodiments, box blurring involves applying a linear spatial filter to each frame to spatially average pixels in the frame and remove noise from the frame. In some embodiments, the detection algorithm removes remaining noise from the linear spatial filtered frames by applying a Gaussian noise filter to each linear spatial filtered frame to remove remaining Gaussian noise from the frame.

By way of example, FIG. 7 conceptually illustrates a block diagram of a mobile device 40 used, in connection with the personal carotid artery stenosis detection and stroke prevention device, to detect carotid artery stenosis in a user in some embodiments. As shown in this figure, the mobile device 40 includes a bus 42, a random access memory (RAM) 44, a main control unit (MCU) 46 for runtime processing of the top and bottom thirty-second video clips and the individual frames, a code execution unit 48 embedded within the MCU 46 to carry out instructions of the mobile app-implemented personal carotid artery stenosis detection and stroke prevention runtime process 30, a first persistent flash memory 50 that stores the captured thirty-second video clips recorded along the top of the user's neck 22B and the bottom of the user's neck 22B, a second persistent flash memory 52 that stores the mobile app implementation of the personal carotid artery stenosis detection and stroke prevention runtime process 30 which is executed by code execution unit 48 of the MCU 46 to run the frame splitting, blurring, and noise filtering operations of the mobile app to determine whether stenosis is present or not. In some embodiments, the mobile app visually outputs the results of the determination of whether stenosis is present on the touchscreen display and interface 54. Additionally, the mobile device 40 may include an input/output (I/O) management unit 56 configured to receive the video clips from the personal carotid artery stenosis detection and stroke prevention device 10 as well as one or more graphics processing units (GPUs) 58 which may be employed in processing the video frames to determine color intensity and perform other processor-intensive operations in connection with the mobile app implementation of the personal carotid artery stenosis detection and stroke prevention runtime process 30.

Notably, all potential users will benefit by way of the relatively low cost of the device. Furthermore, with a low cost for ownership (e.g., about $40), users will be able to use the device routinely without having to pay any money (e.g., co-pays, etc.). Possible additional costs for ownership of the device would involve potentially having to purchase more LEDs or batteries for the LEDs.

In this specification, the terms "software", "program", "algorithm", "application", and the like, are not meant to refer exclusively to mobile application implementations of the personal carotid artery stenosis detection and stroke prevention runtime process 30, but are also meant to include firmware residing in read-only memory or applications stored in magnetic storage, which can be read into memory for processing by a processor, such as a processor of a single board computer (SBC) component of the personal carotid artery stenosis detection and stroke prevention device 10 or a processor of a cloud server that hosts a carotid artery stenosis detection and stroke prevention cloud application service to which the personal carotid artery stenosis detection and stroke prevention mobile app connects for processing and analysis of the top and bottom video clips to determine whether stenosis is present. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

By way of example, FIG. 8 conceptually illustrates an electronic system 60 with which some embodiments of the invention are implemented. The electronic system 60 may be a mobile device, such as the mobile device 40, described above by reference to FIG. 7, a single board computer (SBC) or an embedded in-device controller capable of triggering camera and lighting operations, a server, a cloud server that hosts a cloud application service, or any other sort of electronic device capable of receiving captured video clips and storing the clips for processing, transmitting video clips and/or video streams, processing of video clip frames to determine whether stenosis is present or not, or storing results in the cloud for users of a carotid artery stenosis detection and stroke prevention cloud application service. Such an electronic system includes various types of computer readable media and interfaces for various other types of computer readable media. As shown in this figure, the electronic system 60 includes a main system bus 62, a central processing unit (CPU) 64, a system memory 66, a read-only memory (ROM) 68, a permanent storage device 70, input/output (I/O) interface 72, graphics processing unit(s) (GPUs) 74 that connects to the main system bus 62 through a PCIe bus connecting through the I/O interface 72, and a network 76. Furthermore, when the electronic system 60 is a component, such as a single board computer (SBC) or a controller, of the personal carotid artery stenosis detection and stroke prevention device 10, the electronic system 60 may control the camera 14A and camera lens 14B by way of camera controller 78. Similarly, the electronic system 60 may also control the button lights 18 by way of a lighting controller 80 that is connected through the I/O interface 72. Additionally, a software-implemented personal carotid artery stenosis detection and stroke prevention runtime program 82 ("software program 82") may be installed on the electronic system 60. While the software program 82 may be stored in the permanent storage device 70, it is shown here for exemplary purposes. In particular, the personal carotid artery stenosis detection and stroke prevention runtime program 82 may include the detection algorithm for determining whether stenosis is present. The software program 82 may run directly on the electronic system 60 when, for example, the electronic system 60 is a single board computer or controller component of the personal carotid artery stenosis detection and stroke prevention device 10. In that configuration, the software program 82 may transmit the results to the personal carotid artery stenosis detection and stroke prevention mobile app running on the user's mobile device, thereby allowing the user to view the results. On the other hand, when the electronic system 60 is a cloud server that hosts the carotid artery stenosis detection and stroke prevention cloud application service, the personal carotid artery stenosis detection and stroke prevention mobile app may transmit the top and bottom video clips to the cloud application service for processing/analysis. The carotid artery stenosis detection and stroke prevention cloud application service, in turn, may transmit the results of the processing/analysis back to the personal carotid artery stenosis detection and stroke prevention mobile app running on the user's mobile device. In this way, the user may view the results of whether stenosis is detected or not.

The main system bus 62 collectively represents all system, peripheral, and chipset buses that communicatively connect the numerous internal devices of the electronic system 60, accept for a PCIe bus connected in support of GPUs 74. Besides the GPUs 74, the main system bus 62 communicatively connects the CPU 64 with the ROM 68, the system memory 66, and the permanent storage device 70.

From these various memory units, the CPU 64 retrieves instructions to execute and data to process in order to execute the processes of the invention. For instance, the software program 82 is loaded into the ROM 68 and initialized for execution on the CPU 64, which may be a single processor or a multi-core processor in different embodiments.

The read-only-memory (ROM) 68 stores static data and instructions that are needed by the CPU 64 and other modules of the electronic system 60. The permanent storage device 70, on the other hand, is a read-and-write memory device. The permanent storage device 70 is a non-volatile memory unit that stores instructions and data even when the electronic system 60 is off. For instance, the permanent storage device 70 may store top and bottom video clips, individual (split) frames, and results data that indicated whether stenosis is present or not. Some embodiments of the invention use a mass-storage device (such as a magnetic or optical disk and its corresponding disk drive) as the permanent storage device 70.

Other embodiments use a removable storage device (such as a floppy disk or a flash drive) as the permanent storage device 70. Like the permanent storage device 70, the system memory 66 is a read-and-write memory device. However, unlike permanent storage device 70, the system memory 66 is a volatile read-and-write memory, such as a random access memory. The system memory 66 stores some of the instructions and video/frame/image data that the CPU 64 needs at runtime. In some embodiments, the software implemented code for the software program 82 is stored in the system memory 66, the permanent storage device 70, and/or the ROM 68. For example, the various memory units may include instructions for processing the top and bottom video clips, splitting the video clips into several frames/images, applying blurring and filtering to each of the frames, and comparing the intensities of the frames to detect stenosis in accordance with some embodiments. From these various memory units, the CPU 64 retrieves instructions to execute, transmits instructions and video/frame image data to the GPUs 74 for massively parallel processing in some embodiments.

The main system bus 62 also connects to the input/output interface 72, which itself connects to the lighting controller 80 and the camera controller 78 in connection with the camera 14A and camera lens 14B. When the electronic system 60 is deployed as an embedded component of the personal carotid artery stenosis detection and stroke prevention device 10, such as an embedded SBC or controller, and not deployed as a cloud server that hosts the carotid artery stenosis detection and stroke prevention cloud application service, the I/O interface 72 provides the input/output pathway for all video/frame/image data incoming for processing and all command output for controlling the button lights 18 when the camera 14A and camera lens 14B are capturing the video clips. However, when the electronic system 60 is deployed as a cloud server hosting the carotid artery stenosis detection and stroke prevention cloud application service, then no computing device is embedded as a component of the personal carotid artery stenosis detection and stroke prevention device 10, and video/frame/image processing and analysis are performed by the personal carotid artery stenosis detection and stroke prevention mobile app running on the user's mobile device. Conventionally, other input devices may connect to the I/O interface 72 as is typical, including alphanumeric keyboards and pointing devices (also called "cursor control devices"). Furthermore, other output devices may connect to the electronic system 60 via the I/O interface 72 including devices configured to display the video clips captured by the camera 14A and the results determined by the detection algorithm. Examples of such other output devices include printers and display devices, such as liquid crystal displays (LCD) and organic light emitting diode (OLED) displays. Some embodiments include devices such as a touchscreen that functions as both input and output devices.

Finally, as shown in FIG. 8, bus 62 also couples electronic system 60 to a network 76 through a network adapter (not shown). In this manner, the computer can be a part of a network of computers (such as a local area network ("LAN"), a wide area network ("WAN"), or an intranet), or a network of networks (such as the Internet). Any or all components of electronic system 60 may be used in conjunction with the invention.

These functions described above can be implemented in digital electronic circuitry, in computer software, firmware or hardware. The techniques can be implemented using one or more computer program products. Programmable processors and computers can be packaged or included in other computing device forms, such as single board computers or mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIG. 6 conceptually illustrates a personal carotid artery stenosis detection and stroke prevention runtime process 30. The specific operations of the personal carotid artery stenosis detection and stroke prevention runtime process 30 may not be performed in the exact order shown and described. Specific operations may not be performed in one continuous series of operations, and different specific operations may be performed in different embodiments. Furthermore, the personal carotid artery stenosis detection and stroke prevention runtime process 30 could be implemented using several sub-processes, or as part of a larger macro process. Thus, one of ordinary skill in the art would understand that the invention is not to be limited by the foregoing illustrative details, but rather is to be defined by the appended claims.

We claim:

1. A personal carotid artery stenosis detection and stroke prevention device comprising:
   a camera configured to capture video of a carotid artery neck area of a user;
   a handheld housing structure comprising a plurality of panels comprising a camera plate and at least one side panel with a connecting edge and an open edge, wherein the connecting edge of the at least one side panel attaches to the camera plate, wherein the camera is oriented to capture video in a direction toward the open edge to capture video of the carotid artery neck area of the user when the open edge of the housing structure is positioned along an exterior skin surface of the carotid artery neck area of the user;
   lighting secured to the housing and configured to illuminate when the camera captures video of the carotid artery neck area of the user;
   foam cushioning that lines the open edge of the at least one side panel of the housing structure; and
   a mobile application ("mobile app") that implements a detection algorithm configured to analyze the video captured by the camera to detect potential buildup of carotid artery stenosis.

2. The personal carotid artery stenosis detection and stroke prevention device of claim 1 further comprising a plurality of LED button lights, wherein the lighting secured to the housing comprises a first light in the plurality of LED button lights.

3. The personal carotid artery stenosis detection and stroke prevention device of claim 1, wherein the camera comprises a small form factor video camera that is smaller than the handheld housing structure.

4. The personal carotid artery stenosis detection and stroke prevention device of claim 3, wherein the small form factor video camera comprises a high resolution format video camera.

5. The personal carotid artery stenosis detection and stroke prevention device of claim 1, wherein the foam cushioning provides a soft, cushioning exterior to apply to the exterior skin surface of the carotid artery neck area of the user.

6. The personal carotid artery stenosis detection and stroke prevention device of claim 5, wherein the carotid artery neck area is nearby a carotid artery traversal route where a carotid artery of the user traverses vertically within an interior of the neck of the user.

7. The personal carotid artery stenosis detection and stroke prevention device of claim 6, wherein the carotid artery neck area comprises a top carotid artery neck area nearby a top of the carotid artery traversal route and a bottom carotid artery neck area nearby a bottom of the carotid artery traversal route.

8. The personal carotid artery stenosis detection and stroke prevention device of claim 1, wherein the housing structure comprises a rigid 3D filament printed exterior shell that encapsulates the camera and the lighting.

9. The personal carotid artery stenosis detection and stroke prevention device of claim 8, wherein the camera plate comprises an aperture configured to hold the camera in place when inserted into the aperture.

10. The personal carotid artery stenosis detection and stroke prevention device of claim 1 further comprising:
a mobile device on which the mobile app executes at runtime.

11. The personal carotid artery stenosis detection and stroke prevention device of claim 10, wherein the detection algorithm analyzes video captured by the camera based on a difference of color intensity between a top video clip captured by the camera along a top area of the neck and a bottom video clip captured by the camera along a bottom area of the neck.

12. The personal carotid artery stenosis detection and stroke prevention process of claim 11, wherein the top video clip comprises a thirty-second top video clip and the bottom video clip comprises a thirty-second bottom video clip, wherein each second of video in the thirty-second top video clip and the thirty-second bottom video clip comprises a plurality of at least thirty video frames.

13. The personal carotid artery stenosis detection and stroke prevention process of claim 12, wherein the detection algorithm comprises:
splitting the plurality of at least thirty video frames of the thirty-second top video clip into a fractional plurality of top video frames, wherein the fractional plurality of top video frames comprises only one top video frame for each successive sequence of three top video frames of the thirty-second top video clip;
splitting the plurality of at least thirty video frames of the thirty-second bottom video clip into a fractional plurality of bottom video frames, wherein the fractional plurality of bottom video frames comprises only one bottom video frame for each successive sequence of three bottom video frames of the thirty-second bottom video clip;
removing noise from the fractional plurality of top video frames and the fractional plurality of bottom video frames;
measuring intensity of all video frames in the fractional plurality of top video frames and the fractional plurality of bottom video frames;
calculating a top variation of intensity by subtracting a highest intensity measured in a highest intensity top video frame and a lowest intensity measured in a lowest intensity top video frame;
calculating a bottom variation of intensity by subtracting a highest intensity measured in a highest intensity bottom video frame and a lowest intensity measured in a lowest intensity bottom video frame;
calculating a total intensity variation by subtracting the top variation of intensity from the bottom variation of intensity;
determining whether the total intensity variation is less than a threshold difference of 0.25; and
visually outputting, on a touchscreen display of the mobile device, results of the determination of whether the total intensity variation is less than the threshold difference, wherein stenosis is not confirmed to be present when the total intensity variation is less than the threshold difference, wherein stenosis is confirmed to be present when the total intensity variation is equal to or greater than the threshold difference.

14. The personal carotid artery stenosis detection and stroke prevention process of claim 13, wherein removing noise from the fractional plurality of top video frames and the fractional plurality of bottom video frames comprises applying a linear spatial filter to each frame to spatially average pixels in the frame and remove noise from the frame.

15. The personal carotid artery stenosis detection and stroke prevention process of claim 14, wherein removing noise from the fractional plurality of top video frames and the fractional plurality of bottom video frames further comprises applying a Gaussian noise filter to each linear spatial filtered frame to remove remaining Gaussian noise from the frame.

* * * * *